United States Patent
Maltan et al.

(10) Patent No.: US 7,349,741 B2
(45) Date of Patent: Mar. 25, 2008

(54) COCHLEAR IMPLANT SOUND PROCESSOR WITH PERMANENTLY INTEGRATED REPLENISHABLE POWER SOURCE

(75) Inventors: Albert A Maltan, Sistrans (AT); David Miller, London (GB); William V Harrison, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 477 days.

(21) Appl. No.: 10/675,375

(22) Filed: Sep. 30, 2003

(65) Prior Publication Data

US 2004/0073275 A1 Apr. 15, 2004

Related U.S. Application Data

(60) Provisional application No. 60/417,973, filed on Oct. 11, 2002.

(51) Int. Cl.
*A61N 1/05* (2006.01)
(52) U.S. Cl. .................. 607/57; 381/312; 381/23.1; 607/55; 607/56; 607/60; 607/61; 607/33; 607/137; 128/898
(58) Field of Classification Search ............ 607/55–57, 607/60–61, 33, 136–137; 128/898; 381/312, 381/23.1
See application file for complete search history.

(56) References Cited

U.S. PATENT DOCUMENTS

| 3,942,535 A | 3/1976 | Schulman |
| 4,006,748 A | 2/1977 | Schulman |
| 4,041,955 A | 8/1977 | Kelly |
| 4,134,408 A | 1/1979 | Brownlee |
| 4,379,988 A | 4/1983 | Mattatall |
| 4,532,930 A * | 8/1985 | Crosby et al. ............ 607/57 |

(Continued)

FOREIGN PATENT DOCUMENTS

WO WO-98/37926 A1 9/1998

(Continued)

OTHER PUBLICATIONS

Hansaton Akustik GMBH, Product Brochures and Technical Information, Stueckenstrasse 48—D-22081 Hamburg, Germany, www.hansaton.de, (2001-2002).

(Continued)

*Primary Examiner*—Carl Layno
*Assistant Examiner*—Deborah Malamud
(74) *Attorney, Agent, or Firm*—Henricks, Slavin & Holmes LLP (57) ABSTRACT

A cochlear implant sound processor is powered by a rechargeable battery that is permanently integrated into the sound processor. The sound processor contains an inductive coil that may be tuned to an external charging coil for battery recharging. The electronic circuits and coil of the sound processor are housed in a material transparent to RF signals. The sound processor may be placed in a recharging base station in which the sound processor is positioned in a space surrounded by the inductive charging coil embedded in a material transparent to RF signals. The inductive charging coil sends power to the coil inside the processor and thereby recharges the battery. An alternative embodiment utilizes contacts in the sound processor case and aligned terminals in the recharging base station that allow direct charging of the battery.

25 Claims, 5 Drawing Sheets

U.S. PATENT DOCUMENTS

| | | | |
|---|---|---|---|
| 4,918,736 A * | 4/1990 | Bordewijk | .......... 381/315 |
| 5,279,292 A | 1/1994 | Baumann | |
| 5,314,451 A | 5/1994 | Mulier | |
| 5,411,537 A | 5/1995 | Munshi | |
| 5,411,538 A | 5/1995 | Lin | |
| 5,603,726 A | 2/1997 | Schulman et al. | |
| 5,610,494 A | 3/1997 | Grosfilley | |
| 5,626,629 A | 5/1997 | Faltys et al. | |
| 5,702,431 A | 12/1997 | Wang | |
| 5,824,022 A | 10/1998 | Zilberman et al. | |
| 5,906,635 A | 5/1999 | Maniglia | |
| 6,067,474 A | 5/2000 | Schulman | |
| 6,129,753 A | 10/2000 | Kuzma | |
| 6,219,580 B1 | 4/2001 | Faltys et al. | |
| 6,249,704 B1 | 6/2001 | Maltan | |
| 6,265,100 B1 | 7/2001 | Saaski | |
| 6,272,382 B1 | 8/2001 | Faltys | |
| 6,289,247 B1 | 9/2001 | Faltys et al. | |
| 6,304,787 B1 | 10/2001 | Kuzma | |
| 6,308,101 B1 | 10/2001 | Faltys | |
| 6,310,960 B1 | 10/2001 | Saaski | |
| 6,394,947 B1 | 5/2002 | Leysieffer | |
| 6,415,185 B1 | 7/2002 | Maltan | |
| 6,556,870 B2 | 4/2003 | Zierhofer | |
| 6,658,124 B1 | 12/2003 | Meadows | |
| 6,786,860 B2 | 9/2004 | Maltan | |
| 6,807,445 B2 | 10/2004 | Baumann | |
| 6,842,647 B1 | 1/2005 | Griffith | |
| 6,862,805 B1 | 3/2005 | Kuzma | |
| 6,879,695 B2 | 4/2005 | Maltan | |
| 6,879,855 B2 | 4/2005 | Schulman | |
| 2002/0076071 A1 * | 6/2002 | Single | .......... 381/312 |
| 2002/0120332 A1 | 8/2002 | Law et al. | |
| 2003/0086583 A1 | 5/2003 | Maltan et al. | |

FOREIGN PATENT DOCUMENTS

WO      WO-03/030772 A2    4/2003

OTHER PUBLICATIONS

Griffith, et al. inventors for AB-151U; U.S. Appl. No. 09/981,252, filed Oct. 16, 2001; entitled "Implantable Neural Stimulator System Including Remote Control Unit For Use Therewith".

* cited by examiner

COCHLEAR IMPLANT SOUND PROCESSOR WITH PERMANENTLY INTEGRATED REPLENISHABLE POWER SOURCE

The present application claims the benefit of U.S. Provisional Patent Application Ser. No. 60/417,973, filed Oct. 11, 2002, which application is incorporated herein by reference in its entirety.

FIELD OF THE INVENTION

The present invention relates to hearing aid prosthesis devices, and, in a preferred embodiment, to a cochlear implant system having an external sound processor with a permanently integrated replenishable power source, e.g., a rechargeable battery.

BACKGROUND OF THE INVENTION

All contemporary cochlear implant systems require two separate components: (1) an implant that is implanted in the skull, and (2) a sound (or speech) processor that resembles a hearing aid and is worn on the outside of the body. The two components are linked through RF communication, and operating power for the implant is supplied by the sound processor and transmitted inductively.

The power source in the sound processor consists of either rechargeable or primary batteries. Typical battery operating times for current cochlear implant systems are between 4 hours and 3 days. When battery power is depleted, the cochlear implant user has to physically remove the empty battery from the sound processor and replace it with a new one. This creates several problems:

(1) The small size of the batteries requires good manual dexterity for changing them, which is a problem especially for the many cochlear implant users who are elderly.
(2) Batteries are a choking hazard for small children.
(3) Cochlear implant users have to carry spare batteries with them at all or most times.
(4) The sound processor has to contain a battery compartment that can be either removed entirely for recharging, or that has to have a mechanical latch or door for replacement of the batteries. The mechanical components required increase the size of the processor, and contribute a potential failure mechanism.

It is thus apparent that what is needed is a sound processor for use with a cochlear implant system, or other hearing-aid system, that avoids or minimizes the above-problems.

SUMMARY OF THE INVENTION

The present invention addresses the above and other needs by providing a cochlear implant sound processor that is powered by a rechargeable battery that is permanently integrated into the sound processor. The size and capacity of the battery is such that operating time of the system exceeds a full day. The sound processor contains an inductive coil that may be tuned to an external charging coil when the rechargeable battery needs to be recharged. The material in which the electronic circuits and coil of the sound processor are housed, e.g., plastic, epoxy, or ceramic, is transparent to RF signals. During nighttime, the sound processor is placed in a recharging base station in which the sound processor is positioned in a space surrounded by the inductive charging coil, which coil is also embedded in a material that is transparent to RF signals. The inductive charging coil sends power to the coil inside the processor and thereby recharges the battery. Alternatively, or conjunctively, the sound processor contains a connector, or contacts, that allow direct connection with an external charging source, e.g., the charging source within the base station, when the rechargeable battery needs to be recharged. Advantageously, the cochlear implant user never has to remove or handle the battery directly, and the need for a battery compartment and/or battery connection mechanism is eliminated.

Additionally, the inductive coil embedded in the sound processor can also be used for sending programming information to the programming device, e.g., a laptop computer or other processor in which appropriate programming software has been loaded, thereby eliminating the need for a physical programming connector on the sound processor.

Advantageously, the sound processor may be controlled through use of a small remote control that communicates with the circuits inside of the sound processor via an RF and/or magnetic link, thereby eliminating the need for manual controls (switches, buttons, dials, etc.) on the sound processor. This further allows the case of the sound processor to be effectively closed, or sealed, thereby preventing (or at least minimizing) foreign contaminating particles, e.g., dust or moisture, from entering the sound processor.

A sound processor that has its own integrated power source and the ability to be recharged and programmed through RF in accordance with the present invention may be worn or carried in several locations outside the body, including behind the ear, clipped to the users hair or article of clothing, hanging from a necklace, carried in a shirt or blouse pocket, etc. Alternatively, such a sound processor may be implanted in the skull alongside the currently implanted electronic portion of the cochlear implant system.

A sound processor having its own integrated power source in accordance with the present invention also advantageously avoids the need to replace small batteries, or adjust small controls on the device, thereby eliminating the need for good manual dexterity in use of the device. As a result, the device is much more user friendly for the elderly or others who lack good manual dexterity.

A sound processor having its own integrated power source in accordance with the present invention further eliminates the need for the user to carry spare batteries. Moreover, because no batteries of any kind are needed (except for the remote control, which may be of the conventional AA or AAA size, and are long-lasting), there are no spare or other batteries lying around which could pose a choking hazard for young children.

Finally, a sound processor having its own integrated power source in accordance with the present invention may be made much smaller and be more reliable than equivalent units that use replaceable batteries. According to the present invention, the extra components needed to support a removable battery—mechanical latches or doors, connectors, etc.—may be eliminated, allowing the size of the sound processor to be smaller and removing potential failure mechanisms.

In a preferred embodiment, the integrated power source comprises a rechargeable battery. However, other replenishable power sources may also be used, e.g., ultra or super capacitors, in place of a rechargeable battery, or to supplement a rechargeable battery.

Additionally, it should be noted that as battery technology improves (or compatible technology associated with other power sources becomes available), and as the cost of manufacturing the circuits within a sound processor decreases, a point will some day be reached where it makes economic sense to make a disposable (or recyclable) external sound processor. That is, when the energy capacity of the power source within the sound processor is such that the device can be reliably operated for one or two or more weeks, and the cost of manufacturing and/or recycling the sound processor has been sufficiently reduced, then the user can simply be provided with a supply of body-worn sound processors. When the integrated power source of a given sound processor has been depleted, then the user simply starts using a new sound processor and throws the depleted sound processor away, or (more preferably) sends the depleted sound processor back to the manufacturer for recycling.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
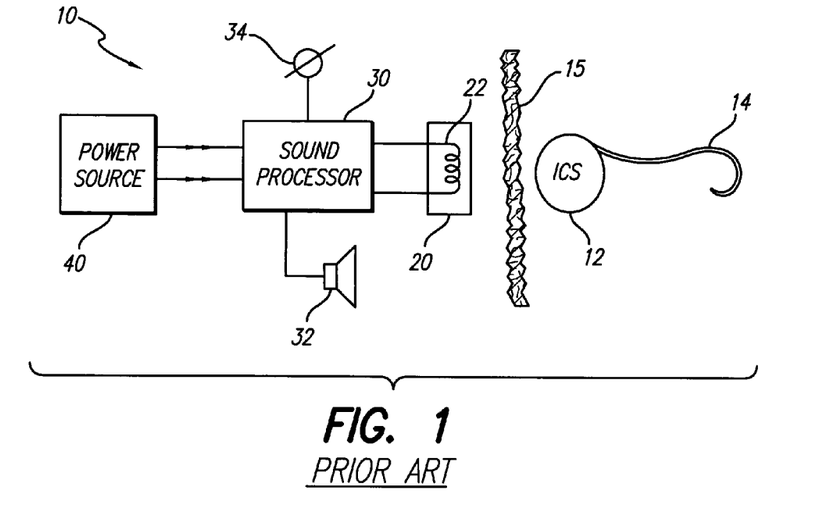
FIG. 1 is a block diagram of a prior art cochlear implant system.

Referring first to FIG. 1, a block diagram of a prior art cochlear implant system 10 is shown. The system 10 includes an implantable cochlear stimulator (ICS) 12 to which an electrode array 14 is attached. The electrode array 14 includes a multiplicity of electrode contacts (not shown) through which electrical stimulation may be applied to tissue and nerves within the inner ear (cochlea) of a user of the device. The ICS 12 and electrode array 14 are designed to be implanted beneath the surface of the skin 15 of the user.

External (not implanted) components of the system 10, also shown in FIG. 1, include a headpiece 20, a sound processor 30 and a power source 40. A microphone 32 is connected to the sound processor 30. Also typically included as part of the sound processor 30 are manual controls 34, usually in the form of knobs or buttons, that allow the user to adjust certain parameters of the sound processor 30.

The power source 40 is detachable from the sound processor 30 and provides the operating power for the system 10. The power source 40 typically comprises primary batteries that can be thrown away when depleted and replaced with new batteries, or rechargeable batteries that can be recharged.

The sound processor 30 receives sound signals through the microphone 32 and processes such signals to convert them to stimulation signals in accordance with a selected speech processing mode that is programmed into the sound processor. The resulting stimulation signals are then applied to a coil 22 in the headpiece 20.

The coil 22 of the headpiece 20 is coupled, either inductively or through an RF link, to another coil (not shown) in the ICS 12, thereby allowing the stimulation signals to be received by the ICS. The stimulation signals typically comprise a carrier signal (which, when received in the ICS is rectified and used to provide operating power for the ICS circuits) that is modulated with control information, i.e., information that designates which electrode contacts are to receive a stimulating pulse, and the intensity and timing of such pulse.

A more complete description of representative cochlear stimulation systems may be found in U.S. Pat. Nos. 5,603, 726; 5,824,022; 6,219,580; and 6,289,247, each of which is incorporated herein by reference. A more detailed description of a representative cochlear electrode array 14 that may be used with a cochlear stimulation system may be found in U.S. Pat. No. 6,129,753, also incorporated herein by reference.

The sound processor 30 used with a cochlear stimulation system 10 may comprise a body-worn device, e.g., one that is fastened to the user by way of a belt clip, or carried in a pocket of the user, or one that is positioned behind the ear of the user.

Figure 2:
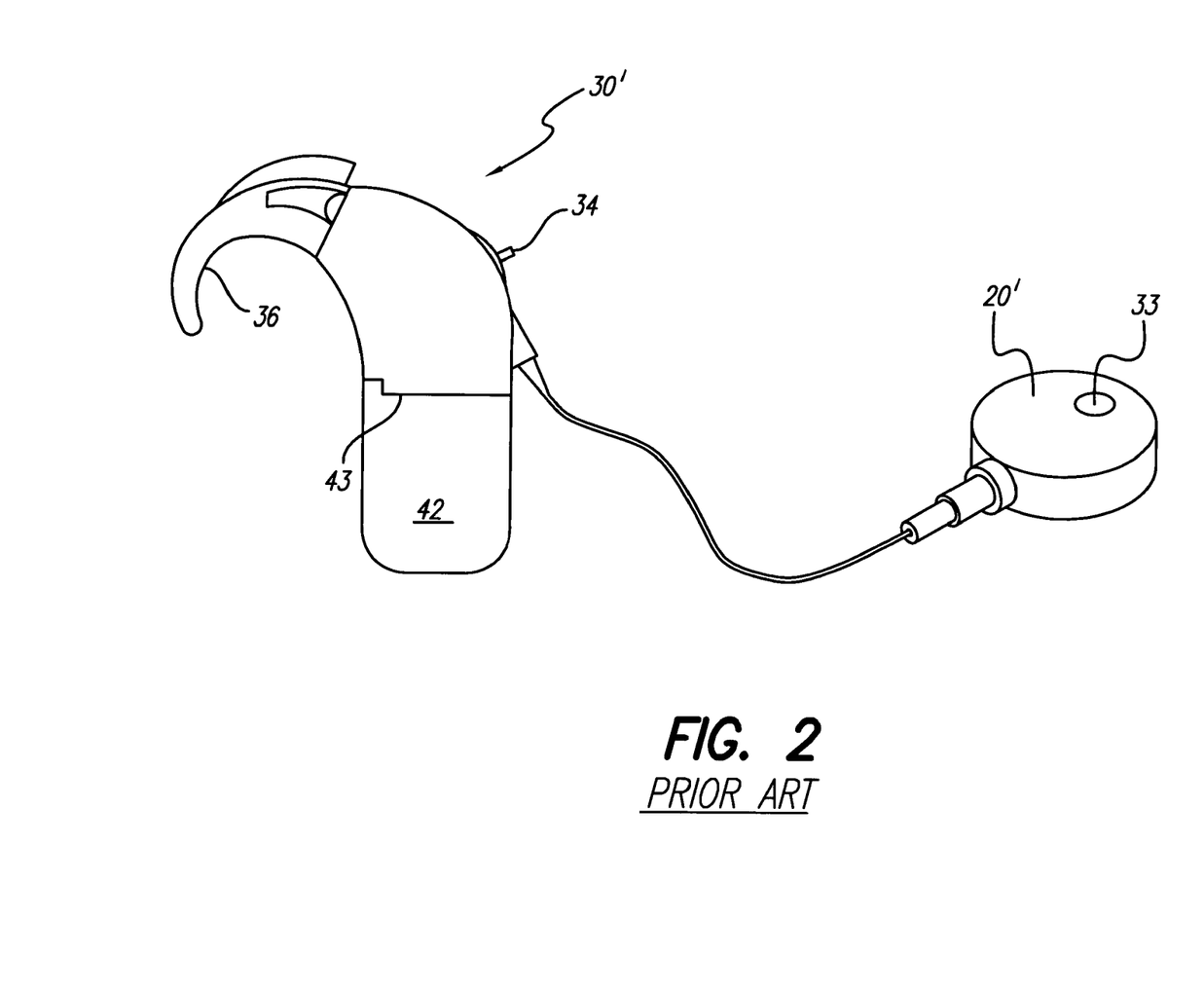
FIG. 2 shows a representative prior art behind-the-ear (BTE) sound processor with its associated headpiece.

FIG. 2 shows a representative prior art behind-the-ear (BTE) sound processor 30' with its associated headpiece 20'. A microphone may be carried within the headpiece 20', with sound passing through a suitable opening 33 of the headpiece to the microphone. Alternatively, the microphone may be built-in to the BTE sound processor 30', or connected to the sound processor 30'. Manual controls 34 are typically located along a back edge of the BTE unit 30'. The BTE sound processor 30' includes an ear hook 36 that allows the body of the processor 30' to be hung behind the ear of the user. A detachable battery door, or battery module 42, is located at the lower portion of the body of the processor 30'. A boundary line 43, emphasized as a heavy line in FIG. 2, defines where the battery door begins. Typically, there is a latch, or other mechanism, that allows the door to be opened when the battery carried therein needs to be removed and replaced. Additionally, because the battery is replaceable, there must be suitable contacts, or connectors, inside the battery compartment that allow the battery, or battery module, to make reliable electrical contact with the sound processing circuits housed within the main body portion of the sound processor 30'. Such latches or mechanisms, as well as the contacts, or connectors, all constitute additional elements that could misalign, malfunction or break, thereby adversely impacting the reliability of the BTE unit 30', as well as components that take up valuable space within the sound processor, thereby rendering the BTE unit 30' larger and more complex and perhaps heavier than it needs to be.

Figure 3:
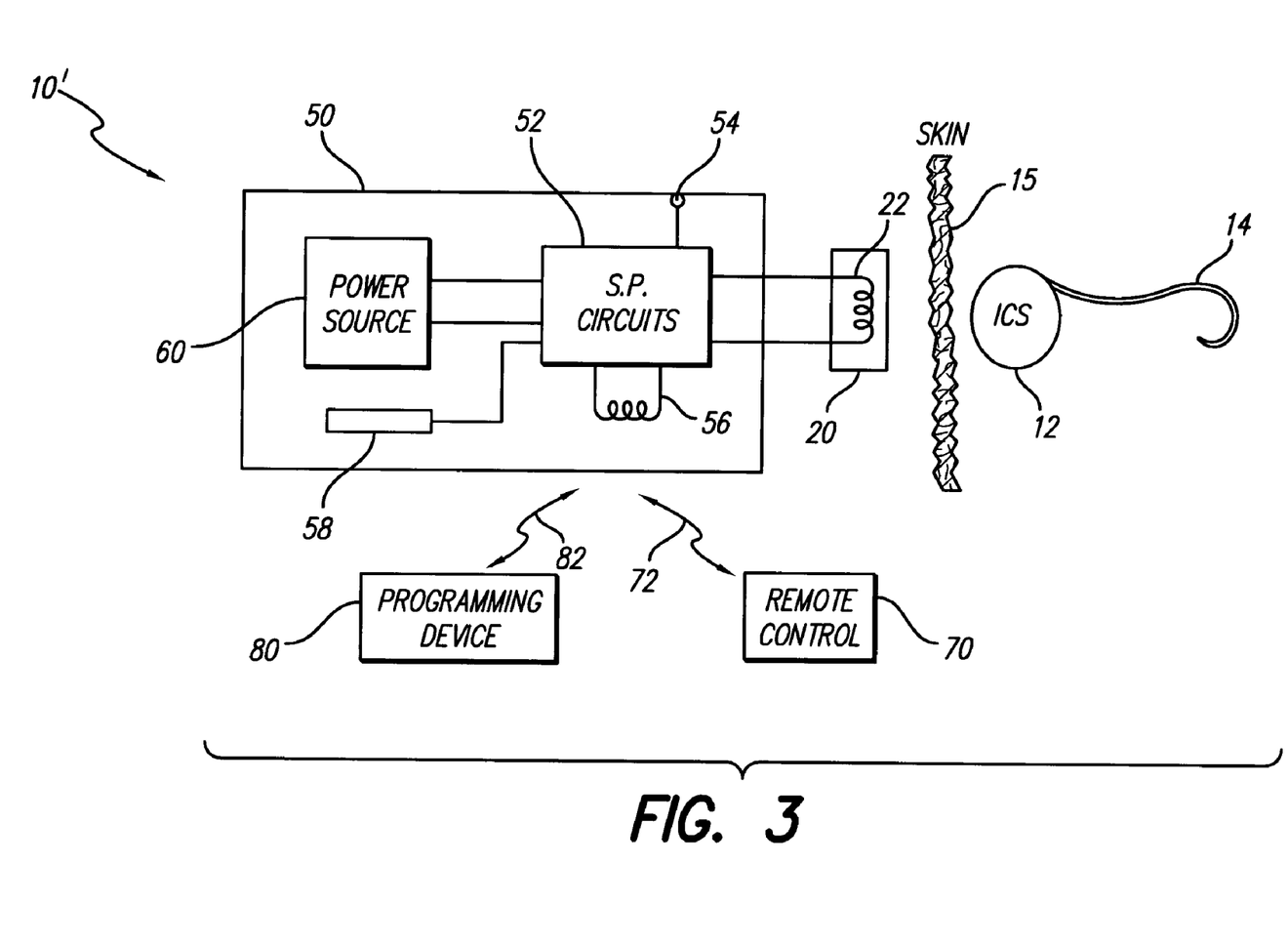
FIG. 3 is a block diagram of an externally-worn sound processor with integral replenishable power source made in accordance with the present invention.

FIG. 3 is a block diagram of an externally-worn sound processor 50 made in accordance with the present invention. The sound processor 50 includes sound processing circuits 52 coupled to a suitable microphone 54, or other sound source, and a headpiece 20. Also included as part of the sound processor 50 is a replenishable power source 60 that is integral with, i.e., included within, the sound processor 50.

A charging/communication coil 56 and one or more sensor modules 58 are additionally included as an integral part of the sound processor 50.

The replenishable power source 60, in a preferred embodiment, comprises a rechargeable Lithium-Ion battery. Other types of rechargeable batteries may also be used. The Lithium-Ion battery is preferred, based on present battery technology, because of its high energy-density characteristics, and its ability to receive numerous recharges. A suitable Lithium-Ion battery for this BTE sound processor application may be obtained from Quallion of Sylmar, Calif.

Still with reference to FIG. 3, the charging/communication coil 56 provides a means through which a charging signal may be received from an external source for the purpose of recharging the power source 60. Such coil 56 also provides a means through which a radio frequency (RF) link 72 may be established between the sound processor 50 and a remote control device 70 and/or a radio frequency (RF) link 82 may be established between the sound processor 50 and a programming device 80. Alternatively, some embodiments of the invention may utilize a remote control device 70 and/or a programming device 80 that establishes an optical link, e.g., an infra-red link, with the sound processor 50, or an acoustic link, e.g., an ultrasound or other acoustic link. An example of one type of remote control device 70 that could be used with the invention is disclosed, e.g., in U.S. patent application Ser. No. 09/981,252, filed Oct. 16, 2001, incorporated herein by reference, which application is assigned to the same assignee as is the present application.

The remote control device 70 provides a means whereby the user may change the operating parameters of the sound processor 50 without the need for manual controls, as have been used in the past. Advantageously, the remote control device 70 may be very small so it can be carried on a key chain, worn on a necklace, or held in a pocket or coin purse. Alternatively, or conjunctively, a relatively large remote control device 70 may be provided that has easy-to-read large controls thereon that can be easily seen and used by the elderly, or others who may neither have good eyesight nor good manual dexterity.

The programming device 80 allows programming of the sound processor 50 and ICS 12. Typically, the programming device 80 is a laptop computer, hand held computing device, or equivalent processor, or is an interface unit that is coupled to a suitable computer. Through use of such device, all of the key operating parameters of the cochlear implant system 10 may be set and monitored, as is known in the art. See, e.g., U.S. Pat. Nos. 5,626,629; 6,219,580 and 6,289,247, incorporated herein by reference.

It is thus seen from FIG. 3 and its accompanying description that a cochlear implant system 10' made in accordance with the present invention includes: (1) an implantable portion 12; (2) an external portion comprising the headpiece 20 and the sound processor 50; (3) a remote control unit 70 adapted to electromagnetically communicate through a recharging/control coil 56 so as to allow operating parameters of the sound processing circuits to be selectively adjusted; and (4) a base station 90 (see FIG. 5) having recharging circuitry housed therein adapted to recharge the rechargeable battery of the sound processor 50 through the recharging/control coil 56 when the sound processor 50 is placed in close proximity to the base station 90. It is further seen that the sound processor 50 comprises the microphone 54, the sound processing circuits 52, the rechargeable battery 60 and a recharging/control coil 56 integrally housed within a closed case.

It is further seen from FIG. 3 and its accompanying description that a sound processor 50 made in accordance with the present invention includes: (1) a microphone 54 adapted to receive sound signals and convert them to electrical signals; (2) a sound processing circuit 52 adapted to receive the electrical signals from the microphone 54 and convert them to a stimulation signal, and further adapted to generate a power signal; (3) a headpiece 20 connected to the sound processing circuit 52 through which the stimulation signal and the power signal are transferred by a coil 22 to an implantable cochlear stimulator 12; (4) a replenishable power source 60 integrally housed within the sound processor 50 that provides operating power for the sound processing circuit 52 and implantable cochlear stimulator 12; and (5) a coil 56 integrally included within the sound processor 50 and coupled to the sound processing circuit 52 and replenishable power source 60 through which power from an external charging source is selectively received to recharge the replenishable power source 60 when the sound processor 50 is in proximity to the external charging source. Moreover, it is seen that the coil 56 and sound processing circuit 52 are further adapted to receive external control signals from an external source that control the operation of the sound processing circuits 52.

Figure 4:
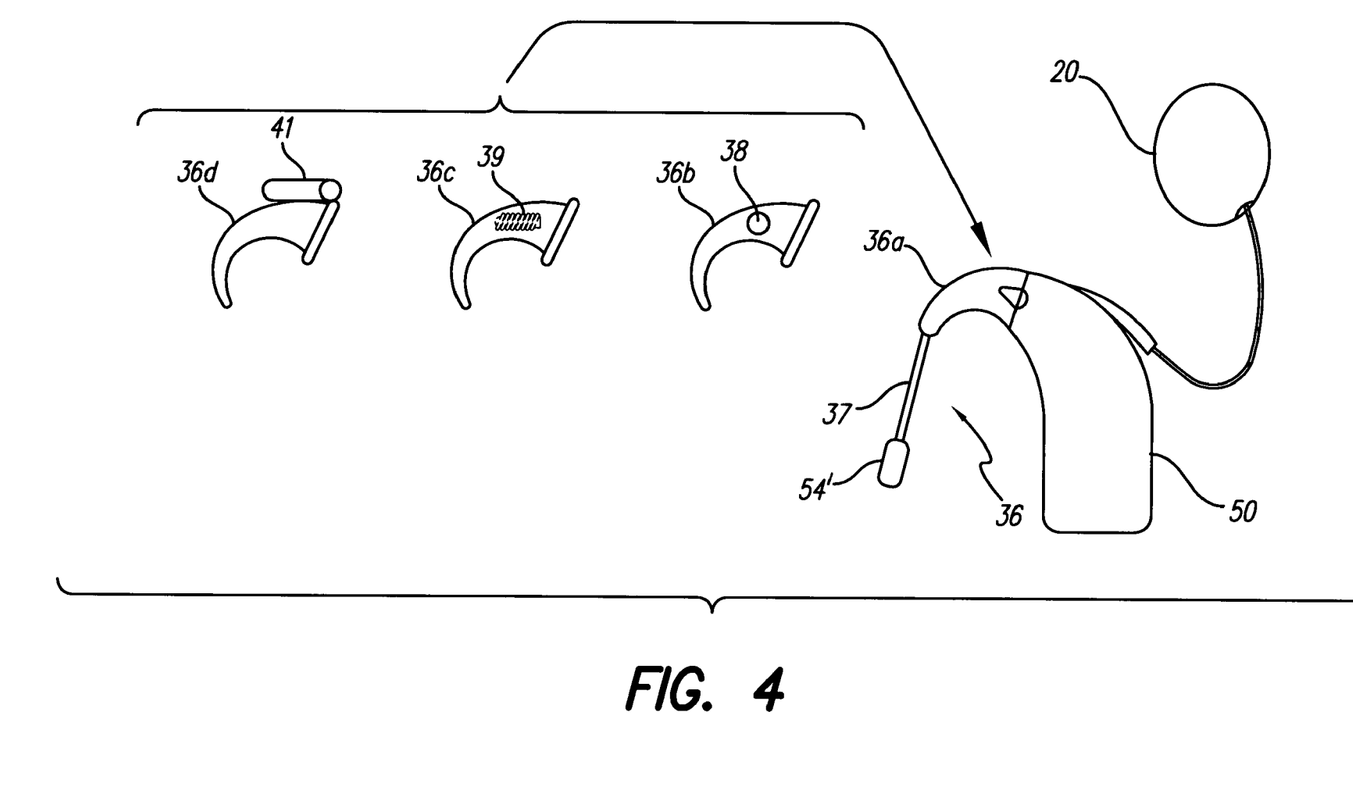
FIG. 4 shows the sound processor with integral power source of the present invention and further illustrates various detachable interface modules that may be used therewith.

FIG. 4 shows a plan view of the sound processor 50 of the present invention, and further illustrates various detachable interface modules that may be used therewith. As seen in FIG. 4, in one embodiment, the ear hook 36 comprises a detachable microphone assembly 36a. Such assembly 36a includes a microphone 54' at the end of a boom 37. The assembly 36a may be detachably secured to the upper end of the sound processor 50, either with a snap-on connection or a screw-on connection.

A second interface module 36b that may be detachably secured to the sound processor 50 comprises a module that includes a visual indicator 38, e.g., a light emitting diode (LED), that provides visual confirmation of the functionality of the sound processor 50. Such module 36b is particularly well suited for very young users who may not be able to communicate regarding how well the system is working. The parents and teachers of such young users can, by looking at the indicator 38, determine whether or not the cochlear implant system is ON and functioning.

A third interface module 36c that may be detachably secured to the sound processor 50 comprises a module that includes a telecoil 39 therein that facilitates telephone communications.

A fourth interface module 36d that may be detachably secured to the sound processor 50 comprises a module that includes a miniature telephone jack 41, or other suitable connector, for connecting with an auxiliary device, e.g., the headphone connection of a CD player, MP3 player, radio, TV, Cell phone, computer, or other handheld audio device.

Figure 5:
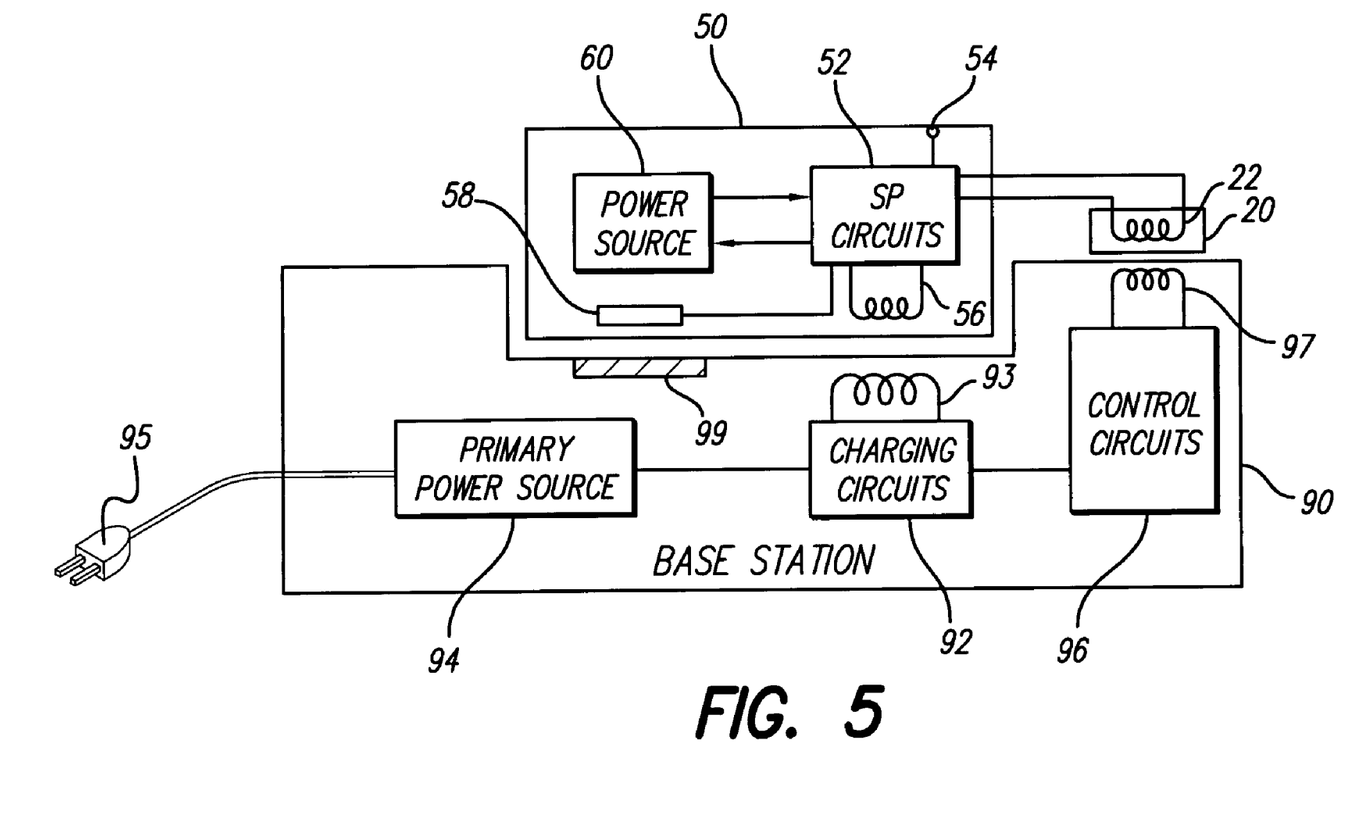
FIG. 5 depicts the manner in which the integral power source of the sound processor may be recharged using a base station.

FIG. 5 depicts the manner in which the integral power source 60 of the sound processor 50 may be recharged using a base station 90. The embodiment of the base station 90 shown in FIG. 5 includes a primary power source 94, which may comprise a primary battery, e.g., a conventional "D" size battery or combination of "D" size batteries, or which may comprise a power supply connected through a plug 95 with a suitable ac power source. In some embodiments, both a primary battery and an ac power source may be used, with the battery providing the operating power used by the base station (including the power transferred to the power source 60 of the sound processor 50) when no ac power source is available, as might occur, for example when the user is traveling or when there is a power outage.

Also included in the base station 90 is a charging circuit 92 that receives power from the primary power source and inductively transfers such power through a coil 93 in the base station to the coil 56 in the sound processor 50. The circuits 52 in the sound processor 50 direct such received power to the power source 60 when the sound processor 50 is placed in close proximity to the base station. The sensor 58 included in the sound processor 50 senses when the Processor 50 is placed in close proximity to the base station. In one embodiment, the sensor 50 comprises a magnetic reed switch that is activated by a small permanent magnet 99 mounted in the base station 90. Control circuits 96, also contained within the base station 90, control the charging process based on feedback signals received from the sound processor 50, e.g., through the headpiece 20. In some embodiments, the coil 22 within the headpiece 20 is coupled with a coil 97 in the base station 90 in the same manner as coupling occurs with the coil in the ICS 12 when the sound processor 50 is in use. When thus connected, diagnostic routines may be carried out to check the status of the power source 60, and other circuits, within the sound processor 50. The control circuits 96 may further be connected to one or more visual displays (not shown in FIG. 5) that signal to a user the status (e.g., discharged, charging, charged) of the replenishable power source in the sound processor 50.

Figure 6:
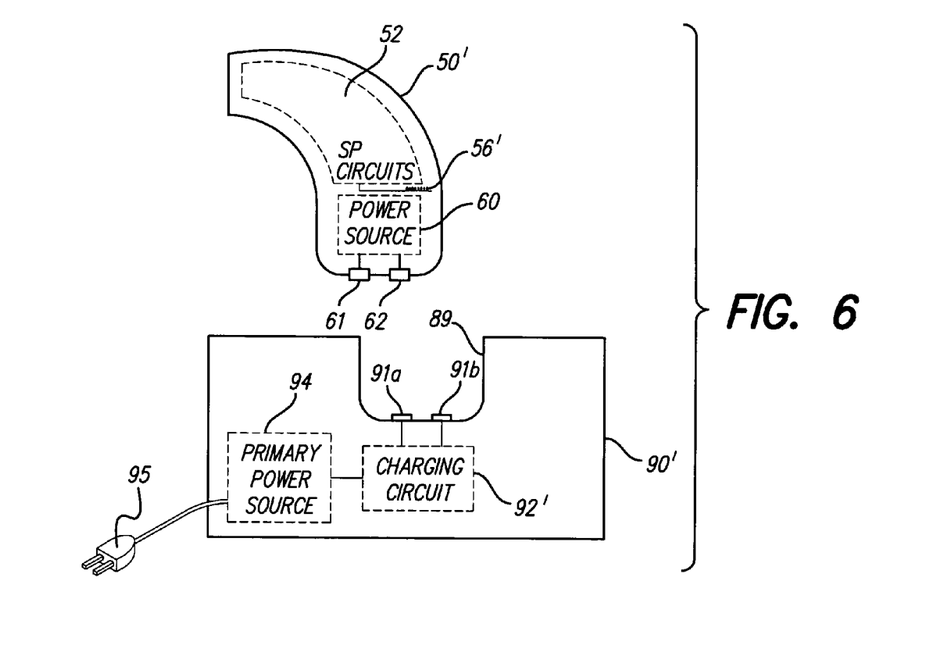
FIG. 6 shows an alternative type of base station that may be used to recharge the power source within the sound processor.

FIG. 6 shows an alternative embodiment of the invention wherein a sound processor 50' contains a power source 60 that is directly connected to contacts 61 and 62 positioned along a bottom edge of the case of the sound processor 50. The sound processor 50' also includes sound processing circuits 52 as previously described. An antenna coil 56' is also embedded within the sound processor 50' in order to allow a remote control unit 70 (FIG. 3) or a programming device 80 (FIG. 3) to establish a communication link with the sound processor 50'. The contacts 61 and 62 may also be used to establish direct electrical connection with the sound processor 50' for purposes other than charging the battery 60, e.g., for programming.

As further seen in FIG. 6, a base station 90' is adapted to receive the sound processor 50'. That is, the base station 90' includes an opening 89, or trough, into which the back end of the sound processor 50' may be inserted. Electrical contacts or terminals 91a and 91b are located in the bottom of the trough 89 and are positioned so as to respectively align with the contacts 61 and 62 of the sound processor 50' when the sound processor 50' is inserted into the trough 89 of the base station 90'. When thus inserted, so that the contacts 61 and 62 make physical and electrical contact with the terminals 91a and 91b, a charging circuit 92' contained within the base station 90' may then monitor the voltage of the power source 60 of the sound processor 50' and control the charge current directed to the power source 60 from a primary power source 94 in an appropriate manner. Such charging can continue as controlled by the charging circuit 92' without the need for additional circuitry within the sound processor 50'.

It is thus seen from FIG. 6, and the above description, that the present invention may be further characterized as a cochlear implant system that comprises an implantable portion 12 and an external portion, wherein the external portion includes a headpiece 20, and a sound processor 50'. The sound processor 50' includes sound processing circuits 52, an antenna coil 56', and a rechargeable battery 60 integrally housed within a closed case. Further, there are electrical contacts 61 and 62 embedded within, or carried on, a surface of the closed case of the sound processor 50'. These electrical contacts connected electrically with the rechargeable battery 60 (and may be connected to other locations within the speech processing circuits 52). The cochlear implant system further includes, although not shown in FIG. 6 (but understood to be part of the system) a remote control unit 70 (see FIG. 3) adapted to electromagnetically communicate through the antenna coil 56' to allow operating parameters of the sound processing circuits 52 to be selectively adjusted. Additionally, the cochlear implant system includes a base station 90' that has a charging circuit 92' and a primary power source 94 and/or 95. The base station 90' also has electrical terminals 91a, 91b that are in electrical contact with the charging circuit 92', and means for holding the sound processor 50' in such a way that the electrical contacts 61, 62 of the sound processor 50' make electrical contact with the terminals 91a, 91b of the base station 90'. When such electrical contact is made between the base station 90' and the sound processor 50', the charging circuit 92' is connected electrically with the rechargeable battery 60, thereby allowing the rechargeable battery 60 of the sound processor 50' to be recharged from the primary power source 94 and/or 95 of the base station 90'.

While the invention herein disclosed has been described by means of specific embodiments and applications thereof, numerous modifications and variations could be made thereto by those skilled in the art without departing from the scope of the invention set forth in the claims.

What is claimed is:

1. A sound processor for use with an implantable cochlear stimulator configured to receive stimulation signals and power from a source external to the implantable cochlear stimulator, the sound processor comprising:
    a microphone configured to receive sound signals and convert them to electrical signals;
    a sound processing circuit configured to receive the electrical signals from the microphone and convert them to a stimulation signal, and further configured to generate a power signal;
    a headpiece connected to the sound processing circuit, the headpiece configured to transfer the stimulation signal and the power signal from the sound processing circuit to the implantable cochlear stimulator; and
    a power source permanently integrated into the sound processor and configured to provide operating power for the sound processing circuit and implantable cochlear stimulator.

2. The sound processor of claim 1 wherein the headpiece comprises a microphone.

3. The sound processor of claim 1 wherein the power source comprises a replenishable power source.

4. The sound processor of claim 3 wherein the replenishable power source comprises a rechargeable battery.

5. The sound processor of claim 4 wherein the rechargeable battery comprises a Lithium-Ion battery.

6. The sound processor of claim 1, further comprising:
    a coil integrally included within the sound processor and coupled to the sound processing circuit and the replenishable power source, the coil configured to selectively receive power from an external charging source and recharge the replenishable power source when the sound processor is in proximity to the external charging source.

7. The sound processor of claim 6 wherein the coil and sound processing circuit are further configured to receive external control signals from an external source that controls the operation of the sound processing circuits.

8. The sound processor of claim 7 further including at least one sensor integrally included therein configured to sense proximity to the external charging source.

9. The sound processor of claim 1, further comprising:
a sound processor case that does not include a power source removal door;
wherein the sound processing circuit and power source are located within the sound processor case.

10. A cochlear implant system comprising:
an implantable portion;
an external portion comprising
a headpiece, and
a sound processor,
wherein the sound processor comprises sound processing circuits, a coil and a battery permanently integrated into a closed case; and
a remote control unit configured to electromagnetically communicate through the coil to allow operating parameters of the sound processing circuits to be selectively adjusted.

11. The cochlear implant system of claim 10 wherein the battery is rechargeable, the cochlear implant system further comprising a base station having recharging circuitry housed therein configured to recharge the rechargeable battery of the sound processor through the coil when the sound processor is placed in close proximity to the base station.

12. The cochlear implant system of claim 11, the external portion further comprising:
a microphone configured to receive sound signals and convert them to electrical signals;
wherein the sound processing circuits are configured to receive the electrical signals from the microphone and convert them to stimulation signals, and further configured to generate power signals; and
wherein the headpiece is connected to the sound processing circuits, the headpiece configured to transfer the stimulation signals and the power signals from the sound processing circuits to the implantable portion.

13. The cochlear implant system of claim 11 wherein the headpiece comprises a microphone.

14. The cochlear implant system of claim 11 wherein the rechargeable battery of the sound processor is configured to provide operating power for the sound processing circuits and the implantable portion.

15. The cochlear implant system of claim 14 wherein the rechargeable battery comprises a Lithium-Ion battery.

16. The cochlear implant system of claim 11 wherein the headpiece comprises a coil and the base station further comprises:
a control circuit coil; and
control circuits, wherein the control circuits are configured to control and monitor the recharging process based on feedback signals received through the control circuit coil from the sound processor through the coil of the headpiece.

17. The cochlear implant system of claim 16 comprising at least one visual display wherein the control circuits are connected to the at least one visual display.

18. The cochlear implant system of claim 10 wherein the closed case does not include a battery removal door.

19. The cochlear implant system of claim 10 wherein the coil comprises a first coil configured to charge the battery and the external portion includes a second coil configured to transmit a power signal to the implantable portion.

20. A cochlear implant system comprising:
an implantable portion;
an external portion comprising
a headpiece, and
a sound processor,
wherein the sound processor includes sound processing circuits, an antenna coil, a rechargeable battery integrally housed within a closed case, and electrical contacts embedded within or carried on an exterior surface of the closed case that are in electrical contact with the rechargeable battery;
a remote control unit configured to electromagnetically communicate through the antenna coil to allow operating parameters of the sound processing circuits to be selectively adjusted; and
a base station comprising a charging circuit and a primary power source, and further having terminals in electrical contact with the charging circuit, and means for holding the sound processor in such a way that the electrical contacts of the sound processor contact the terminals of the base station so that the charging circuit is connected electrically with the rechargeable battery, and so that the rechargeable battery of the sound processor may be recharged from the primary power source of the base station, when the sound processor is held within the base station.

21. The cochlear implant system of claim 20, the external portion further comprising:
a microphone configured to receive sound signals and convert them to electrical signals;
wherein the sound processing circuits are configured to receive the electrical signals from the microphone and convert them to stimulation signals, and further configured to generate power signals; and
wherein the headpiece is connected to the sound processing circuits, the headpiece configured to transfer the stimulation signals and the power signals from the sound processing circuits to the implantable portion.

22. The cochlear implant system of claim 20 wherein the headpiece comprises a microphone.

23. The cochlear implant system of claim 20 wherein the rechargeable battery comprises a Lithium-Ion battery, which battery is configured to provide operating power for the sound processing circuits and the implantable portion.

24. The cochlear implant system of claim 20 wherein the closed case does not include a battery removal door.

25. An external sound processor for use with an implantable cochlear stimulator, the external sound processor comprising:
a microphone configured to receive sound signals and convert them to electrical signals;
a sound processing circuit configured to receive the electrical signals from the microphone and convert them to a stimulation signal that may be received by the implantable cochlear stimulator;
a rechargeable power source permanently connected to the sound processing circuit;
means for mounting the microphone, sound processing circuit and rechargeable power source behind a human ear; and
means, carried by the means for mounting, for transferring power from an external power source to the rechargeable power source.

* * * * *